United States Patent
Lamerichs et al.

(10) Patent No.: US 12,282,079 B2
(45) Date of Patent: Apr. 22, 2025

(54) DETERMINATION OF A SUBJECT SPECIFIC HEMODYNAMIC RESPONSE FUNCTION

(71) Applicant: KONINKLIJKE PHILIPS N.V., Eindhoven (NL)

(72) Inventors: Rudolf Mathias Johannes Nicolaas Lamerichs, Liempde (NL); Timmy Robertus Maria Leufkens, Upplands Vasby (SE); Joanne Henriette Desirée Monique Westerink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/692,096

(22) PCT Filed: Sep. 1, 2022

(86) PCT No.: PCT/EP2022/074297
§ 371 (c)(1),
(2) Date: Mar. 14, 2024

(87) PCT Pub. No.: WO2023/041339
PCT Pub. Date: Mar. 23, 2023

(65) Prior Publication Data
US 2024/0272257 A1    Aug. 15, 2024

(30) Foreign Application Priority Data
Sep. 17, 2021 (EP) ..................................... 21197367

(51) Int. Cl.
G01R 33/48 (2006.01)
A61B 5/055 (2006.01)
(Continued)

(52) U.S. Cl.
CPC .......... G01R 33/4806 (2013.01); A61B 5/055 (2013.01); G01R 33/50 (2013.01); G01R 33/56554 (2013.01)

(58) Field of Classification Search
CPC ................ G01R 33/4806; G01R 33/50; G01R 33/56554; A61B 5/055
See application file for complete search history.

(56) References Cited

U.S. PATENT DOCUMENTS

| 9,116,219 B1 | 8/2015 | Posse |
| 2002/0042563 A1 | 4/2002 | Becerra et al. |

(Continued)

FOREIGN PATENT DOCUMENTS

CN    1626032 A    6/2005

OTHER PUBLICATIONS

Taylor, a., et al., "Characterization of the hemodynamic response function across the majority of human cerebral cortex," Neuroimage. vol 173, 2018. p. 322-331 (Year: 2018).*

(Continued)

*Primary Examiner* — Sean A Frith

(57) ABSTRACT

Disclosed herein is a medical system (100, 300) where execution of machine executable instructions (120) causes a computational system (104) to: receive (200) a time series of a R2-star map (122) for a brain volume (500); receive (202) a stimulus signal (124) descriptive of an occurrence of a sensory stimulus; receive (204) a selection of one or more seed voxels (126) identified in the time series of the R2-star map; calculate (206) a denoised time series of the R2-star map (128); calculate (208) a correlation map (130) between the seed voxels and the denoised time series of the R2-star map; determine (210) an activated region (132) of the brain volume using voxels identified in the correlation map; provide (212) a hemodynamic response (134) function for (Continued)

each voxel and each occurrence of the sensory stimulus; and provide (214) a subject specific hemodynamic response function (136) by averaging the hemodynamic response functions.

19 Claims, 12 Drawing Sheets

(51) Int. Cl.
*G01R 33/50* (2006.01)
*G01R 33/565* (2006.01)

(56) References Cited

U.S. PATENT DOCUMENTS

| | | | |
|---|---|---|---|
| 2005/0197560 A1* | 9/2005 | Rao | A61B 5/055 600/410 |
| 2012/0277572 A1* | 11/2012 | Hubbard | A61B 5/055 600/419 |
| 2014/0275960 A1* | 9/2014 | Hubbard | G01R 33/4806 600/410 |
| 2015/0366482 A1* | 12/2015 | Lee | A61N 1/36053 600/411 |
| 2021/0050109 A1* | 2/2021 | Iacoviello | G16H 20/70 |
| 2021/0369147 A1* | 12/2021 | Cheung | A61B 5/0042 |

OTHER PUBLICATIONS

Sun et al: "Measuring interregional functional connectivity using coherence and partial coherence analyses of fMRI data", Neuroimage, vol. 21, No. 2, Feb. 1, 2004 (Feb. 1, 2004), pp. 647-658, XP055897323,Amsterdam, Nlissn: 1053-8119, DOI:10.1016/j.neuroimage.2003.09.056.

Huang : "Human brain functional areas of unitary pooled activity discovered with fMRI", Scientific Reports vol. 8, No. 1 Feb. 5, 2018 (Feb. 5, 2018), p. 2388.

Lu et al: "Region growing method for the analysis of functional MRI data", Neuroimage, vol. 20, No. 1, Sep. 1, 2003 (Sep. 1, 2003), pp. 455-465, XP055897454,Amsterdam, Nlissn: 1053-8119.

International Search Report and Written Opinion from PCT/EP2022/074297 mailed Nov. 9, 2022.

West et al "BOLD Hemodynamic Response Function Changes Significantly with Healthy Aging" Neuroimage. Mar. 2019 ; 188: 198-207.

Taylor et al "Characterization of the hemodynamic response function across the majority of human cerebral cortex" Neuroimage. Jun. 2018 ; 173: 322-331.

Courtemanche et al "Detecting White Matter Activity Using Conventional 3 Tesla fMRI: An Evaluation of Standard Field Strenght . . . " Neruoimage 169 (2018) p. 145-150.

He et al High Spationtemporal Vessel Specific Hemodynamic Mapping with Multi-echo Single Vessel fMRI Journal of Cerebral Blood Flow and Metabolism 2020 vol. 40 (10) 2098-2114.

Rbrait et al "High Temporal Resolution Functional MRI Using Parallel Echo Volumar Imaging" Journal of Magnetic Resonance Imaging 27 p. 744-753 (2008).

Proulx et al "Increased Sensitivity of fast BOLD fmri with a Subject Specific Hemodynamic Response Function and Application to Epilepsy" Neuroimage 93 (2014) p. 59-73.

Wang et al "The Method of Analyzing fMRI Data Based on Temporal Spatial Correlation Properties" Journal of Circuits and Systems 2003 (06) p. 72-76 English abstract only.

* cited by examiner

DETERMINATION OF A SUBJECT SPECIFIC HEMODYNAMIC RESPONSE FUNCTION

CROSS REFERENCE TO RELATED APPLICATIONS

This application is a U.S. national phase application of International Application No. PCT/EP2022/074297 filed on Sep. 1, 2022, which claims the benefit of EP application Ser. No. 21/197,367.2 filed on Sep. 17, 2021 and is incorporated herein by reference.

FIELD OF THE INVENTION

The invention relates to functional magnetic resonance imaging, in particular to the hemodynamic response function.

BACKGROUND OF THE INVENTION

A large static magnetic field is used by Magnetic Resonance Imaging (MRI) scanners to align the nuclear spins of atoms as part of the procedure for producing images within the body of a subject. This large static magnetic field is referred to as the B0 field or the main magnetic field. Various quantities or properties of the subject can be measured spatially using MRI. Various imaging protocols can be implemented by using pulse sequences to control the acquisition of magnetic resonance data and can be used to measure various properties of a subject.

For example, in functional Magnetic Resonance Imaging (fMRI) brain activity is measured using magnetic resonance imaging. A common type of functional magnetic resonance imaging is blood-oxygen-level dependent (BOLD) contrast. BOLD imaging relies on the properties of oxygenated and deoxygenated hemoglobin. Oxygenated hemoglobin is paramagnetic and deoxygenated hemoglobin is diamagnetic. T2-star weighted pulse sequences can therefore detect changes in the oxygenation of blood in the brain. The BOLD signal is characterized by the hemodynamic response function.

United States patent publication U.S. 9,116,219 B1 discloses a system and methods for high-speed functional magnetic resonance imaging using multi-slab echo-volume imaging (EVI), specifically a combination of multi-slab excitation and single-shot 3D encoding with parallel imaging to reduce geometrical image distortion and blurring, and to increase blood oxygenation level-dependent (BOLD) sensitivity compared to conventional echo-planar imaging (EPI).

SUMMARY OF THE INVENTION

The invention provides for a medical system, a computer program, and a method in the independent claims. Embodiments are given in the dependent claims.

A draw back in performing functional Magnetic Resonance Imaging (fMRI) is that current clinical techniques may assume a constant hemodynamic response function. Embodiments may provide a means of quickly and accurately determining a subject specific hemodynamic response function as disclosed herein. The subject specific hemodynamic response function may have several benefits. Firstly, it may be used to improve the accuracy of subsequent fMRI studies on the same subject. Another advantage, as is illustrated herein, is that the hemodynamic response function varies from individual to individual and may be useful as a diagnostic test.

In one aspect the invention provides for a medical system that comprises a memory that stores machine-executable instructions and a computational system. The computational system could be integrated into different configurations. For example, in one example the computational system may be available over the internet or other network system, for example as a cloud-based system that provides processing or image processing services. In other examples the computational system could be a workstation or other computer system used by a radiologist or other medical professional. In yet other examples, the computational system could be the control system for a magnetic resonance imaging system or be integrated into or a module of the control system for a magnetic resonance imaging system.

Execution of the machine-executable instructions causes the computational system to receive a time series of an R2-star map for a brain volume of a subject. The time series of the R2-star map is a mapping of the R2-star value within the brain volume of the subject. This map is provided as a time series or as a series of these maps that are presented sequentially in time. Execution of the machine-executable instructions further causes the computational system to receive a stimulus signal descriptive of an occurrence of a sensory stimulus repeatedly provided to the subject. The stimulus signal is synchronized to the time series of the R2-star map. A sensory stimulus is a stimulus which is provided to the subject which activates a stimulus of the subject. This may be useful for determining the R2-star values because the sensory stimulus may be something passive that the subject reacts to mentally. For example, in functional magnetic resonance imaging studies the subject can be tasked with performing a mental task. However, the sensory stimulus is something like an auditory or visual signal which is provided to the subject and does not require mental exertion or thought.

Execution of the machine-executable instructions further causes the computational system to receive a selection of one or more seed voxels identified in the time series of the R2-star map. The one or more seed voxels may for example be portions of the brain volume which are identified as being activated by the sensory stimulus. The selection could for example be provided by an automated system or by the selection of an operator. Execution of the machine-executable instructions further causes the computational system to calculate a denoised time series of the R2-star map by applying a temporal filter algorithm to the time series of the R2-star map. For example, the value of the R2-star in a particular voxel can be looked at as a function of time. This time series can be denoised using the temporal filter. A digital filtering algorithm or something as simple as fitting a spline to the R2-star value for a particular voxel may be applied.

Execution of the machine-executable instructions further causes the computational system to calculate a correlation map for each voxel of the one or more seed voxels by calculating a pixel wise calculation between each voxel of the one or more seed voxels and the denoised time series of the R2-star map. That is to say, for each of the one or more seed voxels a correlation map is calculated between that voxel and all of the other voxels in the R2-star map. This may for example be achieved by calculating the correlation coefficient. For a particular voxel there will be a time series of the R2-star value. The correlation coefficient is calculated for the time signal of the R2-star value for each voxel with each voxel of the one or more seed voxels.

Execution of the machine-executable instructions further causes the computational system to determine an activated region of the brain volume by combining voxels identified in the correlation map for each of the voxel of the one or more seed voxels above a predetermined threshold. For example, for each of the one or more seed voxels there is a correlation map between it and the other voxels of the brain volume. Each of these correlation maps can be thresholded and then combined. This may ensure that regions in the brain which are activated by the sensory stimulus are not ignored.

Execution of the machine-executable instructions further causes the computational system to provide a hemodynamic response function for each voxel and each occurrence of the sensory stimulus in the activated region of the brain volume by aligning the time series of the R2-star map with the stimulus signal. The activated regions are the portions of the brain volume which were shown to be in correlation with the one or more seed voxels. The voxels in the activated region are then used to calculate the hemodynamic response function. The stimulus signal indicates whenever the sensory stimulus was provided to the subject. This may be used to take the time signal of the R2-star map for each voxel in the activated region and align these individual response functions together.

Execution of the machine-executable instructions further causes the computational system to provide a subject specific hemodynamic response function by averaging the hemodynamic response function for each voxel on each occurrence of the sensory stimulus in the activated region of the brain volume. For each voxel there will be data descriptive of the hemodynamic response function each time the sensory stimulus occurred. The subject-specific hemodynamic response function is calculated by collecting all of the hemodynamic response functions for each occurrence of the sensory stimulus for each voxel in the activated region and then averaging them.

This embodiment may have the advantage that it provides a subject-specific hemodynamic response function which may be used to evaluate a subject. The subject-specific hemodynamic response function may vary from person-to-person as well as the health state of the person. Having the subject-specific hemodynamic response function may also be very useful because it may enable the performance of other functional magnetic resonance imaging studies more accurately. Typically, during functional magnetic resonance imaging. the hemodynamic response function is assumed to have a particular value. As will be demonstrated later, this is not the case and there can be very large variations between individuals. This variation can be used to study or provide information which may be useful to a physician, as well as was mentioned earlier, provide for more accurate functional magnetic resonance imaging in other studies.

In another embodiment execution of the machine-executable instructions further causes the computational system to calculate a time of maximum value for each of the hemodynamic response functions for each voxel and for each occurrence of the sensory stimulus in the activated region of the brain volume. Execution of the machine-executable instructions further causes the computational system to calculate a statistical property of the time maximum value for each of the hemodynamic response functions for each voxel and for each occurrence of the sensory stimulus in the activated region of the brain volume.

Execution of the machine-executable instructions further causes the computational system to remove any hemodynamic response function from the calculation of the subject-specific hemodynamic response function if it fails to meet a predetermined criteria determined using the statistical property. This for example may be used to remove outlying data. For example. the person may have moved or some of the data may be non-useable or non-relevant. The statistical property could for example be an average or a certain number of standard deviations or a window from a histogram. This may provide a convenient means for improving the quality of the estimate of the subject-specific hemodynamic response function.

In another embodiment the time of the maximum value for each of the hemodynamic response functions for each voxel in each occurrence of the sensory stimulus in the activated region of the brain volume is calculated using a smoothing function. For example. a digital filter or a curve may be fit and used as the smoothing function. For example, a spline may be fit to each of the individual hemodynamic response functions to provide a better estimate of the maximum value.

In another embodiment the machine-executable instructions further causes the computational system to receive multiple acquisitions of EPI multi-echo T2-star weighted k-space data descriptive of the brain volume of the subject. The multiple acquisitions are synchronized to the stimulus signal. Execution of the machine-executable instructions further causes the computational system to receive T1-weighted k-space data descriptive of the brain volume of the subject. Execution of the machine-executable instructions further causes the computational system to reconstruct a T1-weighted image of the brain volume from the T1-weighted k-space data. Execution of the machine-executable instructions further causes the computational system to reconstruct a T2-star weighted image for each echo of the multiple acquisitions of EPI multi-echo T2-star weighted k-space data.

Execution of the machine-executable instructions further causes the computational system to calculate an aligned T2-star weighted image for each echo of the multiple acquisitions of EPI multi-echo T2-star weighted k-space data by performing pre-processing that aligns the T2-star weighted image for each echo of the multiple acquisitions of EPI multi-echo T2-star weighted k-space data with the T1-weighted image of the brain volume with each other. For example, during the course of the acquisition of the T2-star weighted k-space data the subject may move. The T1-weighted k-space data and the resulting T1-weighted image of the brain volume or one of the T2-start weighted images may be used as a reference to correct for this motion.

Execution of the machine-executable instructions further causes the computational system to calculate the time series of the R2-star map for the brain volume of a subject for each voxel by fitting a curve to the aligned T2-star weighted image for each echo of the multiple acquisitions of the EPI multi-echo T2-star weighted k-space data. The data for the multiple echoes may be used to calculate the decay rate and thereby the R2-star value for each voxel. This may be advantageous because it may provide for an extremely accurate estimate of the R2-star value for particular voxels.

In another embodiment the calculation of the aligned T2-star weighted image for each echo of the multiple acquisitions of EPI multi-echo T2-star weighted k-space data is performed by preprocessing that aligns the T2-star weighted image for each echo of the multiple acquisitions of EPI multi-echo T2-star weighted k-space data with the T1-weighted image of the brain volume with each other comprises the following steps: the first is to co-register a chosen image corresponding to a first echo of a chosen acquisition of the multiple acquisitions of EPI multi-echo T2-star weighted k-space data to the T1-weighted image. The next step is to segment the T1-weighted image to produce a gray matter segmentation, a white matter segmentation and a cerebrospinal fluid segmentation.

In a next step the T1-weighted image is re-sliced as well as the gray matter segmentation, the white matter segmentation and the cerebrospinal fluid segmentation to match the chosen image using the co-registration between the chosen image and the T1-weighted image. In this way the datasets are all aligned spatially. In a next step a brain mask is constructed using the gray matter segmentation, the white matter segmentation and the cerebrospinal fluid segmentation. In a final step, the T2-star weighted image for each echo of the multiple acquisitions of EPI multi-echo are realigned with a corresponding image of the chosen image. The brain mask may be used to determine areas which are ignored in the analysis.

In another embodiment the EPI multi-echo T2-star weighted k-space data is descriptive of the brain volume of the subject has k-space data for three echoes. The use of three echoes may be beneficial because it may provide for an accurate determination of the T2-star or R2-star value. The use of only two echoes may result in an inaccurate measurement of the T2-star values. The use of four echoes may not provide a significantly better estimate but may take considerably longer.

In another embodiment the memory further stores EPI multi-echo pulse sequence commands and T1-weighted pulse sequence commands. The medical system further comprises a magnetic resonance imaging system. The medical system further comprises a stimulus system configured 30 to provide the sensory stimulus to the subject. This for example could be a display or projector which provides a visual stimulus to the subject. In other examples the stimulus system may be provided by an auditory or speaker or headphone system. In yet other examples, the sensory stimulus may be a tactile stimulus.

Execution of the machine-executable instructions are further configured to cause the computational system to acquire the T1-weighted k-space data by controlling the magnetic resonance imaging system with the T1-weighted pulse sequence commands. Execution of the machine-executable instructions are further configured to cause the computational system to acquire the multiple acquisitions of EPI multi-echo T2-star weighted k-space data by controlling the magnetic resonance imaging system with the EPI multi-echo pulse sequence commands. And finally, execution of the machine-executable instructions is further configured to cause the computational system to control the stimulus system with the stimulus signal during the acquisition of the multiple acquisitions of EPI multi-echo T2-star weighted k-space data. In some examples, there may be meta data recorded either with the k-space data or elsewhere or clock information which is used to synchronize the stimulus signal with the acquisition of the T2-star weighted k-space data.

In another embodiment the stimulus system is a visual stimulus system. The brain volume comprises the visual cortex. The stimulus signal provided by the stimulus system may be different in different examples. In some cases, the timing of the events in the stimulus signal may be randomly varied to prevent people from counting or anticipating when the stimulus will occur.

In another embodiment the EPI multi-echo pulse sequence commands are single-shot EPI pulse sequence commands. The EPI multi-echo pulse sequence commands are multi-band pulse sequence commands. This has the advantage that the T2-star weighted k-space data may be acquired more rapidly.

In another embodiment execution of the machine-executable instructions further causes the computational system to calculate any one of the following parameters from the subject-specific hemodynamic response function: a maximum amplitude, a time-to-maximum amplitude, an FWHM or full width at half maximum width of the subject-specific hemodynamic response function, a skewedness of the subject-specific hemodynamic response function, an integral of the subject-specific hemodynamic response function, an initial maximum rising slope, a maximum descending slope, and combinations thereof. All of these parameters may be useful in providing possibly diagnostic information descriptive of the subject.

In another embodiment execution of the machine-executable instructions further causes the computational system to receive functional magnetic resonance imaging k-space data descriptive of a brain region of the subject. Execution of the machine-executable instructions further causes the computational system to calculate a functional magnetic resonance image using the functional magnetic resonance imaging k-space data and the subject-specific hemodynamic response function. In this embodiment the subject-specific hemodynamic response function was used to analyze a conventional or reconstruct a conventional functional magnetic resonance image. This may be advantageous because conventionally specific values for the hemodynamic response function are used. However, this is not the case as this function may vary from person-to-person. This embodiment may provide for functional magnetic resonance images of higher quality and/or more accuracy.

In another embodiment execution of the machine-executable instructions further causes the computational system to construct a percentage change mapping from the R2-star map using the stimulus signal. Execution of the machine-executable instructions further causes the computational system to provide the one or more seed voxels by searching for voxels of a predetermined threshold within the percentage change mapping. In this embodiment the event-specific data is used to search for the seed voxels.

In another embodiment the time series of R2-star map comprises block-related R2-star maps. In block-related functional magnetic resonance imaging a stimulus is presented to the subject for a period of time interspaced with resting periods. This may be useful in identifying specific regions of the brain which are activated by a particular stimulus. In this embodiment the block-related R2-star maps are for such time periods. Execution of the machine-executable instructions further causes the computational system to identify the one or more seed voxels by constructing a percentage change mapping from the block-related R2-star maps by calculating a change between resting blocks and stimulus blocks. Execution of the machine-executable instructions further causes the computational system to identify the one or more seed voxels by providing the one or more seed voxels by searching for voxels above a predetermined threshold within the percentage change mapping. This may also be equivalent to searching for a certain number of voxels with the highest value.

In another aspect the invention provides for a method of medical imaging. The method comprises receiving a time series of an R2-star map for a brain volume of a subject. The method further comprises receiving a stimulus signal descriptive of an occurrence of a sensory stimulus repeatedly provided to the subject. The stimulus signal is synchronized to the time series of the R2-star map. The method further comprises receiving a selection of one or more seed voxels identified in the time series of the R2-star map. The method further comprises calculating a denoised time series of the R2-star map by applying a temporal filter algorithm to the time series of the R2-star map. The method further comprises calculating a correlation map for each voxel of the one or more seed voxels by calculating a pixel-wise correlation between each voxel of the one or more seed voxels and the denoised time series of the R2-star map. The method further comprises determining an activated region of the brain volume by combining voxels identified in the correlation map for each voxel of the one or more seed voxels above a predetermined threshold.

The method further comprises providing a hemodynamic response function for each voxel in each occurrence of the sensory stimulus in the activated region of the brain volume by aligning the time series of the R2-star map with the stimulus signal. The method further comprises providing a subject-specific hemodynamic response function by averaging the hemodynamic response function for each voxel and for each occurrence of the sensory stimulus in the activated region of the brain volume. The advantages of this embodiment have been previously discussed.

In another aspect the invention provides for a computer program comprising machine-executable instructions configured for execution by a computational system. The computer program may for example be stored in a memory or storage device such as a non-transitory storage medium.

Execution of the machine-executable instructions causes the computational system to receive a time series of an R2-star map for a brain volume of the subject. Execution of the machine-executable instructions further causes the computational system to receive a stimulus signal descriptive of an occurrence of a sensory stimulus repeatedly provided to the subject. The stimulus signal is synchronized to the time series of the R2-star map. Execution of the machine-executable instructions further causes the computational system to receive a selection of one or more seed voxels identified in the time series of the R2-star map. Execution of the machine-executable instructions further causes the computational system to calculate a denoised time series of the R2-star map by applying a temporal filter algorithm to the time series of the R2-star map.

Execution of the machine-executable instructions further causes the computational system to calculate a correlation map for each voxel of the one or more seed voxels by calculating a pixel-wise correlation between each voxel of the one or more seed voxels and the denoised time series of the R2-star map. Execution of the machine-executable instructions further causes the computational system to determine an activated region of the brain volume by combining voxels identified in the correlation map for each voxel of the one or more seed voxels above a predetermined threshold.

Execution of the machine-executable instructions further causes the computational system to provide a hemodynamic response function for each voxel in each occurrence of the sensory stimulus in the activated region of the brain volume by aligning the time series of the R2-star map with the stimulus signal. Execution of the machine-executable instructions further causes the computational system to provide a subject-specific hemodynamic response function by averaging the hemodynamic response function for each voxel in each occurrence of the sensory stimulus in the activated region of the brain volume. The advantages of this embodiment have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan.

A Magnetic Resonance Imaging (MRI) image or MR image is defined herein as being the reconstructed two- or three-dimensional visualization of anatomic data contained within the k-space data. This visualization can be performed using a computer.

BRIEF DESCRIPTION OF THE DRAWINGS

In the following preferred embodiments of the invention will be described, by way of example only, and with reference to the drawings in which.

DESCRIPTION OF EMBODIMENTS

Like numbered elements in these figures are either equivalent elements or perform the same function. Elements which have been discussed previously will not necessarily be discussed in later figures if the function is equivalent.

Figure 1:
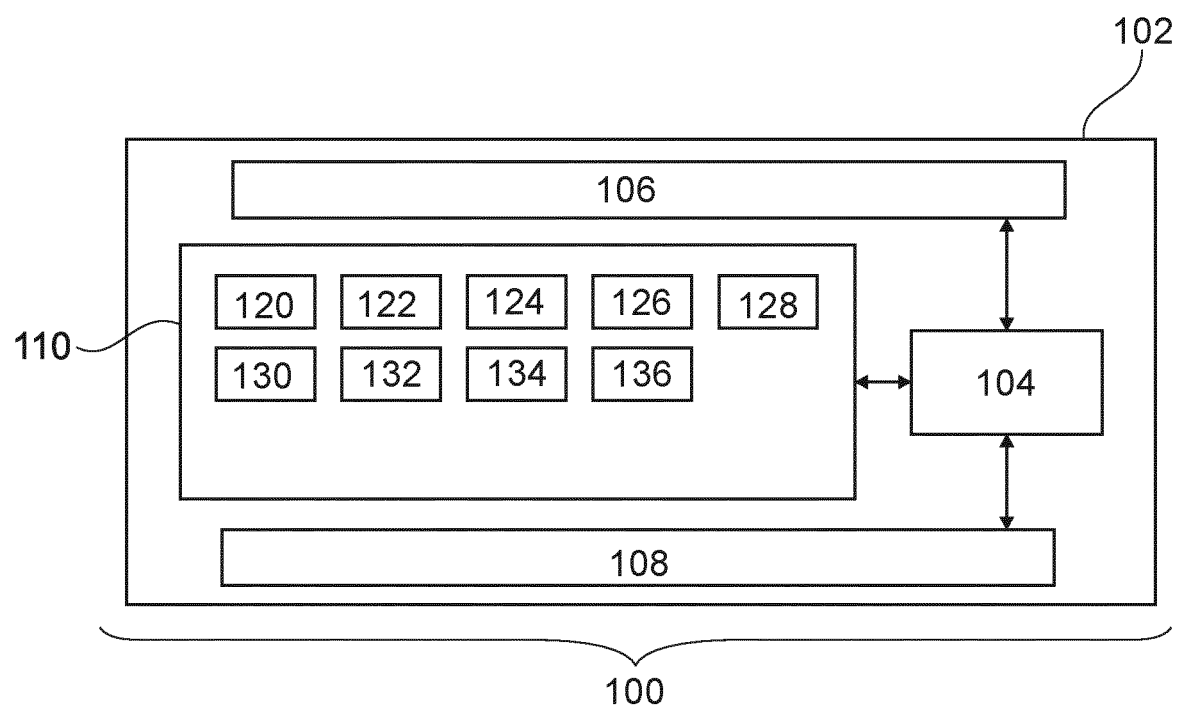
FIG. 1 illustrates an example of a medical system.

FIG. 1 illustrates an example of a medical system 100. In this example the medical system 100 comprises a computer 102 which has a computational system 104. The computer 102 could for example be a distributed computing system as well as a computer located remotely or via a cloud web service. The computer 102 could also be a workstation or computer used by a radiologist or other medical professional. The computer 102 could also be a control system for a magnetic resonance imaging system. The computer 102 is shown as comprising a computational system 104 that is intended to represent one or more computational systems that may be located in one or more locations. The computational system 104 is connected to an optional hardware interface 106 and an optional user interface 108. If present, the hardware interface 106 enables the computational system 104 to control other components of the medical system 100 such as a magnetic resonance imaging system. The user interface 108 may enable an operator to control and operate and interact with the medical system 100.

The computational system 104 is further shown as being in communication with a memory 110. The memory 110 is intended to represent various types of memory which may be able to communicate with the computational system 104. The memory 110 is shown as containing machine-executable instructions 120. The machine-executable instructions 120 enable the computational system 104 to perform various tasks such as controlling other components of the medical system 100 as well as performing numerical and image processing tasks. The memory 110 is further shown as containing a time series of an R2-star map 122 for a brain volume.

The memory 110 is further shown as containing a stimulus signal 124 that is synchronized to the time series of the R2-star map 122. The memory 110 is further shown as containing a selection of one or more seed voxels 126 in the brain volume. The memory 110 is further shown as containing a denoised time series of the R2-star map 128. The memory 110 is further shown as containing correlation maps 130 between the one or more seed voxels 126 and the rest of the voxels in the denoised time series of the R2-star map. The memory 110 is further shown as containing an activation region 132 identified in the brain volume that was found by thresholding the correlation maps 130 and then combining them together.

The memory 110 is further shown as containing hemodynamic response functions 134 for each voxel of the activation region 132 and for each time a stimulus was presented as is indicated in the stimulus signal 124. For example, for one particular voxel there will be a number of hemodynamic response functions 134 each time a stimulus was presented. The memory 110 is further shown as containing a subject-specific hemodynamic response function 136 found by averaging the hemodynamic response functions 134.

Figure 2:
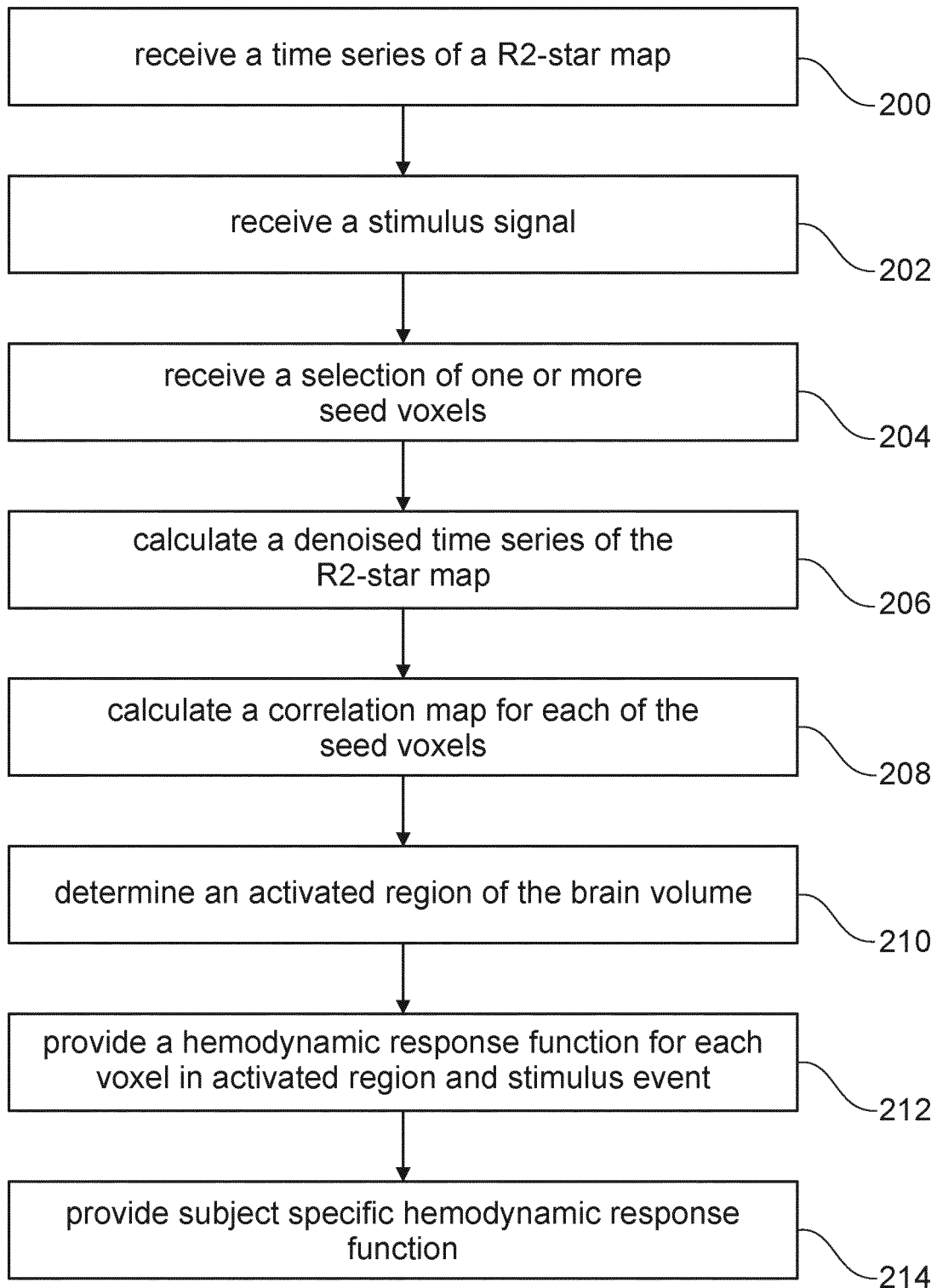
FIG. 2 shows a flow chart which illustrates a method of using the medical system of FIG. 1.

FIG. 2 shows a flowchart which illustrates a method of operating the medical system 100 of FIG. 1. First, in step 200, the time series of the R2-star map 122 is received. Next, in step 202, the stimulus signal 124 is received. As was mentioned before the stimulus signal 124 is synchronized to the time series of the R2-star map 122. The stimulus signal 124 is representative of when a sensory stimulus was provided or presented to the subject using a stimulus generator such as an auditory or visual display. Then, in step 204, the selection of one or more seed voxels 126 is received. This could for example be provided manually by an operator or may be provided via an automated algorithm. Next, in step 206, the denoised time series of the R2-star map 128 is calculated from the time series of the R2-star map 122.

There is a series of R2-star maps. Taking a particular voxel and then taking a value from each of the maps there is a time-based R2-star signal for each voxel. This signal for each of the voxels is then denoised to provide the denoised time series of the R2-star map. This could for example be achieved using the digital filter or by fitting a curve such as a spline to the data. Next, in step 208, the correlation map for each of the selection of one or more seed voxels 126 is calculated. For example, a correlation coefficient between the time signal for each of the one or more seed voxels and the rest of the voxels in the denoised time series R2-star map may be calculated. In step 210 the activated region of the brain volume 132 is than calculated. This is calculated by taking the correlation maps 130 and thresholding them.

Thresholding a single correlation map identifies regions that correlate with a particular seed voxel temporally. The activation region then is the combination of the thresholded correlation maps. Then, in step 212, a hemodynamic response functions 134 are provided for each voxel and each occurrence of the sensory stimulus in the activated region of the brain volume by aligning the time series of the R2-star map with the stimulus signal. Finally, in step 214, the subject-specific hemodynamic response functions 136 is then calculated by averaging the hemodynamic response functions 134. Additional things such as smoothing or curve fitting may also be performed but this is not necessary.

Figure 3:
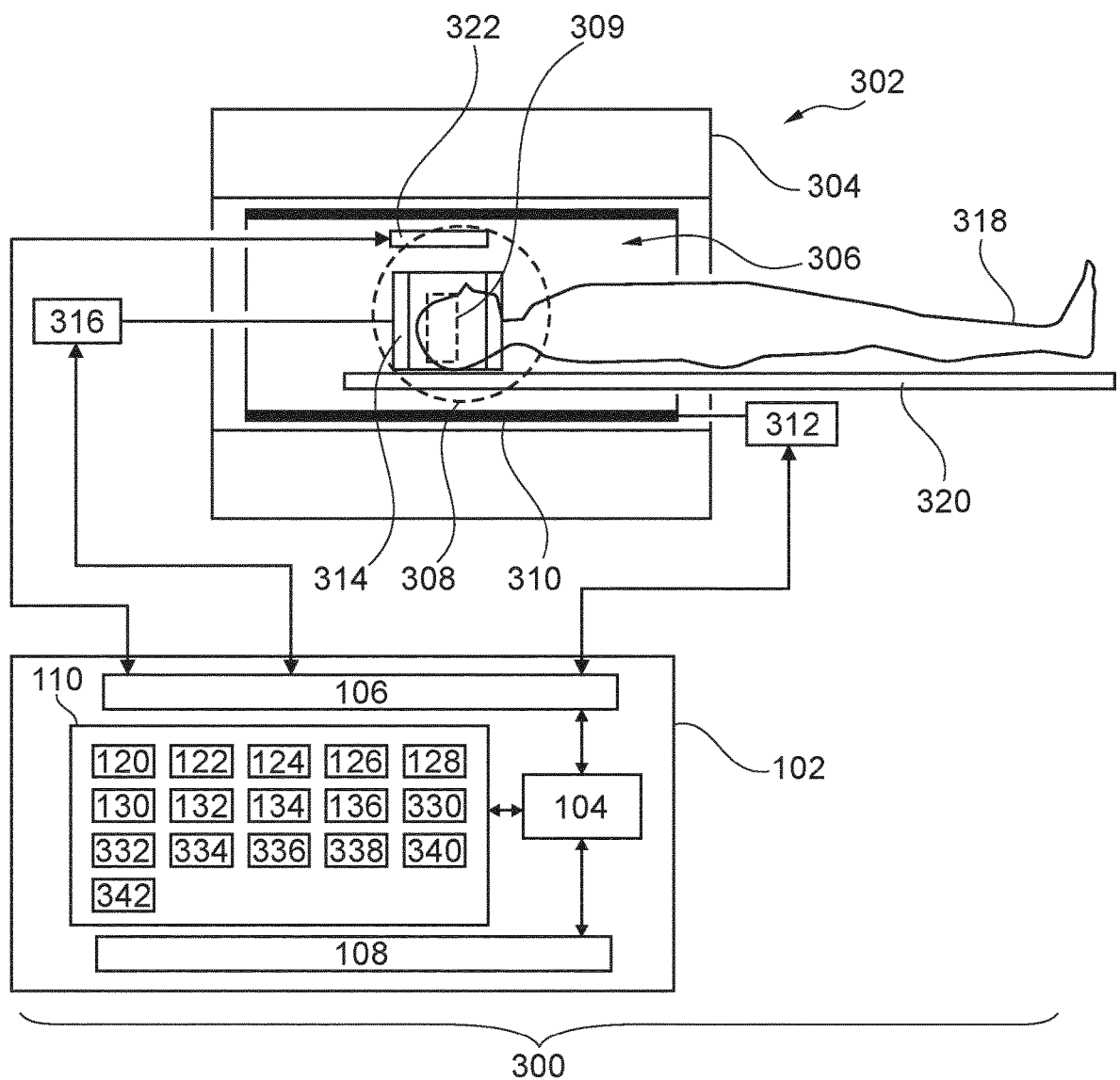
FIG. 3 illustrates a further example of a medical system.

FIG. 3 shows a figure which illustrates a further example of a medical system 300. The medical system 300 is similar to the medical system 100 depicted in FIG. 1 except that it additionally comprises a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A field of view 309 is shown within the imaging zone 308. The magnetic resonance data that is acquired typically acquired for the field of view 309. The field of view 309 is shown as imaging a brain volume more a subject 318 which is shown as being supported by a subject support 320.

Within the imaging zone 308 the head of the subject 318 is within a head coil 314. This enables the imaging of a field of view 309. In some cases, the brain volume will be identical with the field of view 309. In other cases the brain volume will be within the field of view 309. The T1-weighted image could for example have a larger field of view than the EPI multi-echo T2-star weighted images.

Above the head of the subject 318 is a stimulus system 322 which in this example is a display. Various types of displays could be used such as mirrors which reflect a view of a projection outside of the bore 306 of the magnet 304 as well as also providing for a magnetic resonance compatible display directly above the eyes of the subject 318. Other types of stimuli such as sound or also tactile stimulation may also be used.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. In this case the radio-frequency coil 314 is a head coil. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels.

The transceiver 316 and the gradient controller 312 are shown as being connected to the hardware interface 106 of the computer system 102. Both of these components, as well as others such as the subject support supplying positional data, may supply the sensor data 126.

The memory 110 is further shown as containing EPI multi-echo pulse sequence commands which are configured for acquiring EPI multi-echo T2-star weighted k-space data. The memory 110 is further shown as containing T1-weighted pulse sequence commands 332 which are configured for controlling the magnetic resonance imaging system to acquire T1-weighted k-space data. The pulse sequence commands in general are commands which are used to control the magnetic resonance imaging system 302 to acquire k-space data according to a particular magnetic resonance imaging protocol.

The memory 110 is further shown as containing EPI multi-echo T2-star weighted k-space data 334 that has been acquired by controlling the magnetic resonance imaging system 302 with the EPI multi-echo pulse sequence commands 330. The memory 110 is further shown as containing T1-weighted k-space data 336 that has been acquired by controlling the magnetic resonance imaging system 302 with the T1-weighted pulse sequence commands 332. The memory 110 is further shown as containing a T1-weighted image 338 of the brain volume that has been reconstructed from the T1-weighted k-space data 336. The memory 110 is further shown as containing an T2-star weighted image 340 for each echo of the EPI multi-echo T2-star weighted k-space data 334. The memory 110 is further shown as containing an aligned T2-star weighted image 342 for each echo.

Figure 4:
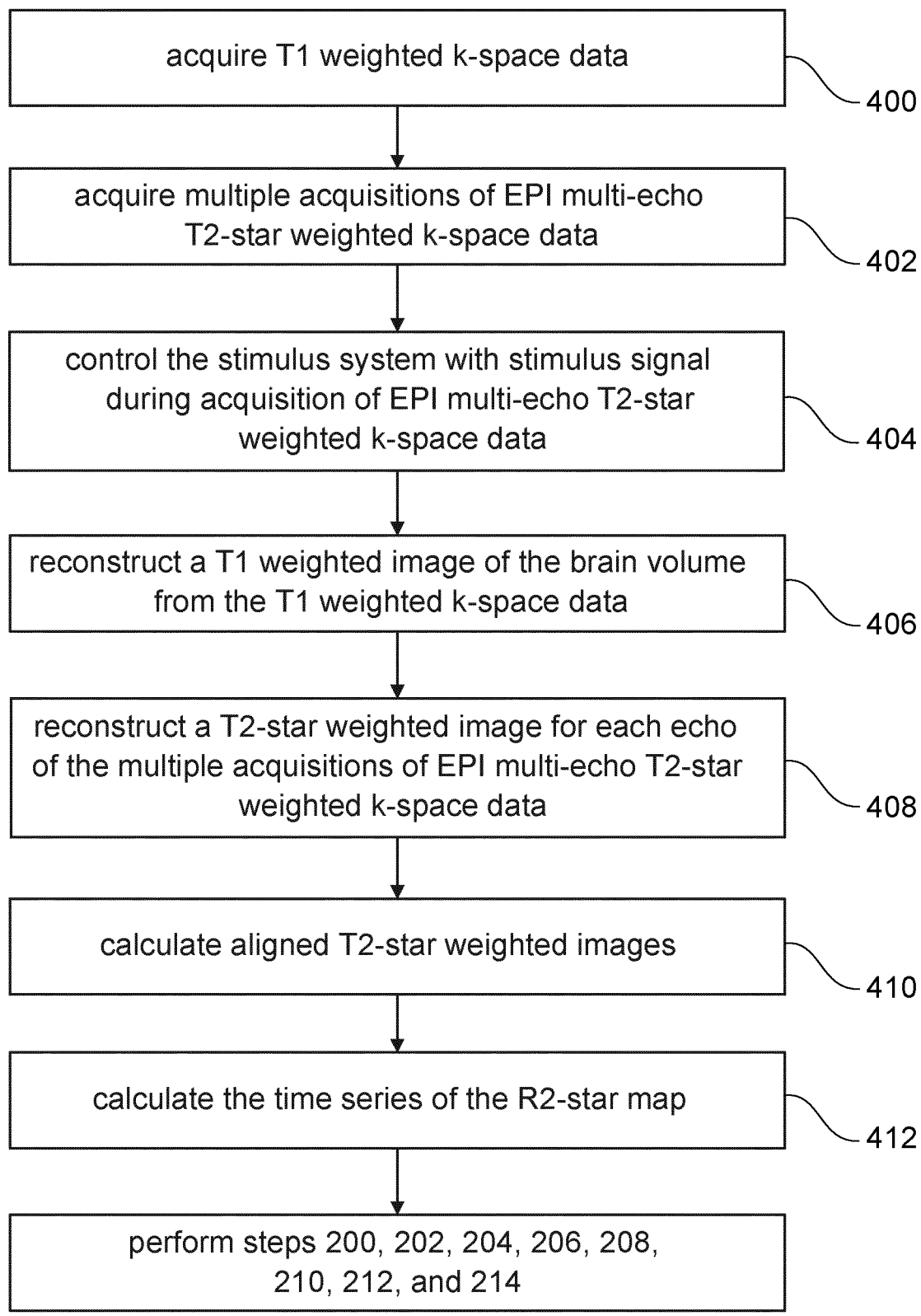
FIG. 4 shows a flow chart which illustrates a method of using the medical system of FIG. 3.

FIG. 4 shows a flowchart which illustrates how to operate the medical system 300 of FIG. 3. First, in step 400, the T1-weighted k-space data 336 is acquired by controlling the magnetic resonance imaging system 302 with the T1-weighted pulse sequence commands 332. Then, in step 402, the multiple acquisitions of the EPI multi-echo T2-star weighted k-space data 334 is acquired by controlling the magnetic resonance imaging system with the EPI multi-echo pulse sequence commands 330 multiple times. During the acquisition of the EPI multi-echo T2-star weighted k-space data 334 multiple times, step 404 is performed. In step 404 the stimulus system 332 is controlled with the stimulus signal 124 to present the sensory stimulus to the subject 318.

The stimulus signal 124 is then synchronized with the various acquisitions of the EPI multi-echo T2-star weighted k-space data 334. Then, in step 406, the T1-weighted image of the brain volume 338 is reconstructed from the T1-weighted k-space data 336. Next, in step 408, an T2-star weighted image is reconstructed for each of the multiple acquisitions of the EPI multi-echo T2-star weighted k-space data 334. Then, in step 410, the aligned T2-star weighted image for each echo 342 is calculated for each echo of the multiple acquisitions of EPI multi-echo T2-star weighted k-space data by performing preprocessing that aligns the T2-star weighted image for each echo of the multiple acquisitions of the EPI multi-echo T2-star weighted k-space data with the T1-weighted image of the brain volume. Next, in step 412, the time series of the R2-star map 122 is calculated for the brain volume of the subject for each voxel by fitting a decay curve to the aligned T2-star weighted image for each echo of the multiple acquisitions of the EPI multi-echo T2-star weighted k-space data. After step 412 is performed the method then proceeds to steps 200-214 as is illustrated in FIG. 2.

Functional fMRI is an important tool in neuroscience and there is increasing interest and evidence that fMRI can be used for diagnostic purposes. In particular, in psychiatric disorders fMRI can prove to be a game changer, e.g., in many cases an anatomical scan does not show any abnormalities in these patients. However, function MRI shown that these patients have aberrant responses, i.e. stronger or weaker response, responses in other areas of the brain. The fMRI responses is a result of hemodynamic variations, the blood flow increases and, also the ratio of oxy- versus deoxyhemoglobin is different in areas that show a response.

The blood flow variation is described by the hemodynamic responses function (HRF). In most analysis tools a constant HRF is used for all subjects. As is illustrated below the HRF functional varies over subjects and that the HRF may have additional diagnostic value.

As disclosed herein, no prior knowledge is used to determine the HRF. A high temporal resolution measurement is made that takes advantage of the multi-echo EPI.

In some examples the method may depends on fMRI data recorded with multi-echo EPI which increases the contrast to noise ratio (CNR) by approx. 30%. Benefits of some examples may include one or more of the following:

Analysis of HRF without prior knowledge
Increased SNR by using multi echo fMRI
High spatial resolution.

fMRI task: In the examples below the subject performed visual tasks: a block design and an event related task. In all experiments, the visual stimulus was a flickering checkerboard. For the block design the duration was 30 s with a flickering frequency of 8 Hz. In total 8 task blocks were recorded interleaved with 30 s resting blocks. The experiment ended with a resting block. In the event related experiment, a checkerboard with a duration of 1 s and a frequency of 10 Hz. was used. The time between the onset of the event was 20 or 30 s, and was randomly varied. The onset times were: 20, 50, 80, 100, 130, 150, 170, 200, 230, 250, 280, 310, 330, 350, 380, 400, 420, 450, 470, 490 s. A total of 20 events were displayed. Both event related runs were identical.

The paradigm was presented visually using a beamer or projector. The exact onset of all stimuli was controlled by a TLL pulse from the scanner.

All MRI experiments were recorded on a 3T MRI system, using a 32-channel head coil. All fMRI experiments had the same parameters settings.

Single shot EPI; Tr=500 ms: echo-time=12, 28, 44 ms; Multi-band acceleration (MB)=3 slices; voxel size=2.75× 2.75×3; 21 slice; 1020 dynamics. Since a short TR was the 'holy grail', the number of slices was the limiting factor. As a result, the fMRI scan did not cover the full brain in the FH direction, field of view (fov) 63 mm.

Figure 5:
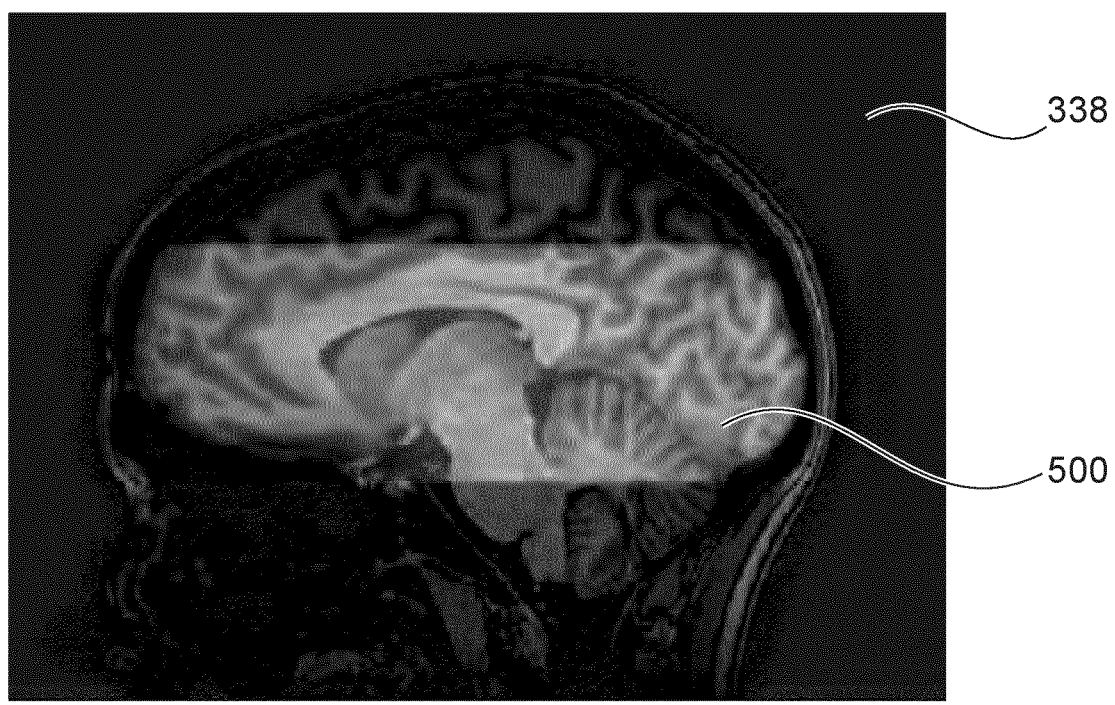
FIG. 5 shows an example of a T1-weighted image.

FIG. 5 shows an example of a T1-weighted (T1w) image 338. Within the T1-weighted image 338 the brain volume 500 is indicated. In this example the brain volume 500 comprises the visual cortex. In the example illustrated, a visual stimulation was used. Time can therefore be saved by limiting the brain volume 500 to the visual cortex. The T1-weighted scan was a Multi shot TFE, Tr/TE=8.3/3.8 ms; 1 mm$^3$ voxel size. The Single shot EPI data was acquired in the brain volume 500.

Figure 6:
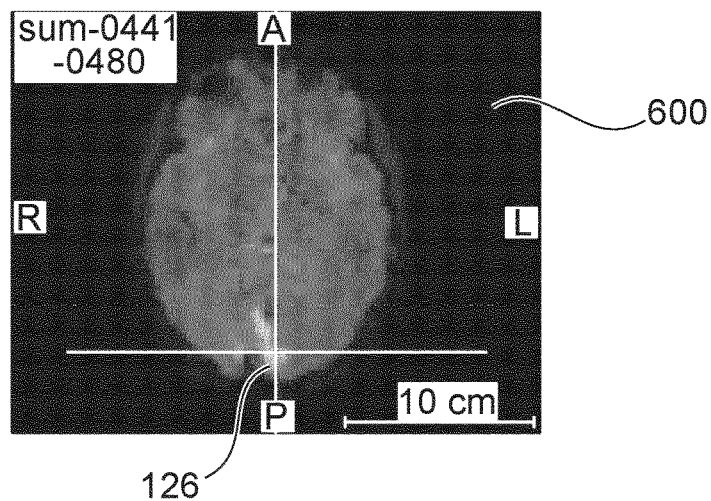
FIG. 6 shows three views of a three-dimensional R2-star image that shows the percent change of activation for a task block.
Figure 6:
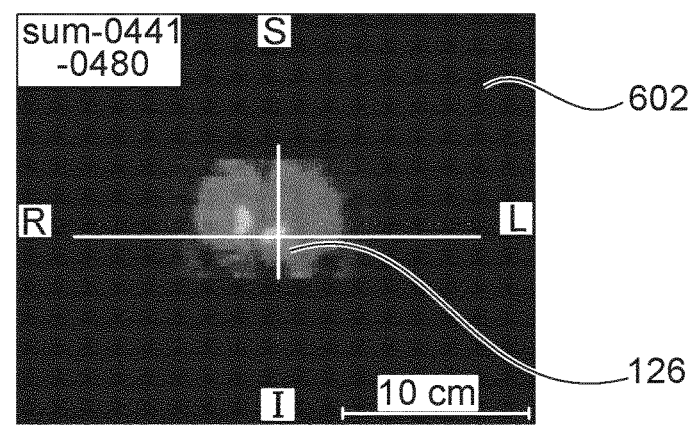
Figure 6:
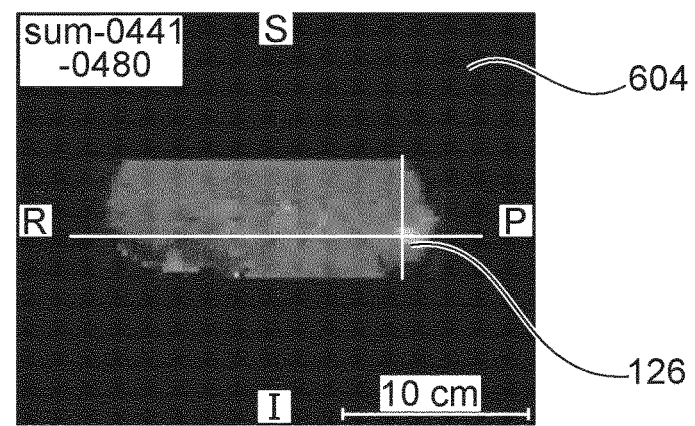

The preprocessing of the fMRI data includes one or more of the following steps performed on the T1w images (the fMRI data) and the T1w image:

1. Co-register the T1w image to first dynamic (first acquisition of the block MRI data) of first echo (of the three). (The choice of using the first dynamic is arbitrary.)
2. Segment the T1 weighted image for grey matter (GM), white matter (WM), and cerebral spinal fluid (CSF) (SPM segmentation)
3. Reslice the T1w image and segmentation to match the first dynamic of echo-1 (SPM reslice)
4. Construct masks from the segmentations that so that there is a mask for the GM and the whole brain.
5. Realign each echo of the fMRI data separately to the first dynamic (SPM realignment)
6. Perform a linear detrend of the fMRI data
7. Smooth the fMRI data using a Gaussian kernel, FWHM 5 (SPM)
8. fMRI: perform a log linear fit of the echoes using the fMRI data to create 4D-R2-star and 4D-S0 maps. Data outside of the whole brain mask is excluded.
10. fMRI: construct functional activation map for the block-task as PSC based on the R2-star maps FIG. 6 shows three views 600, 602, 604 of a three-dimensional R2-star image that shows the percent change of activation for a task block. These images were used to manually select the seed voxel 126. This seed voxel 126 is marked in all three images. FIG. 6 shows percent signal change (PSC) of activation of task block 4 from the R2-star data The HRF responses have been selected as follows:
1) Manually choose one or two seed voxels in the activated area (block paradigm), see FIG. 6.
2) Select the time course of the chosen voxels in the event-related data.
3) Apply a smoothing spline to these seed voxels FIG. 7.

Figure 7:
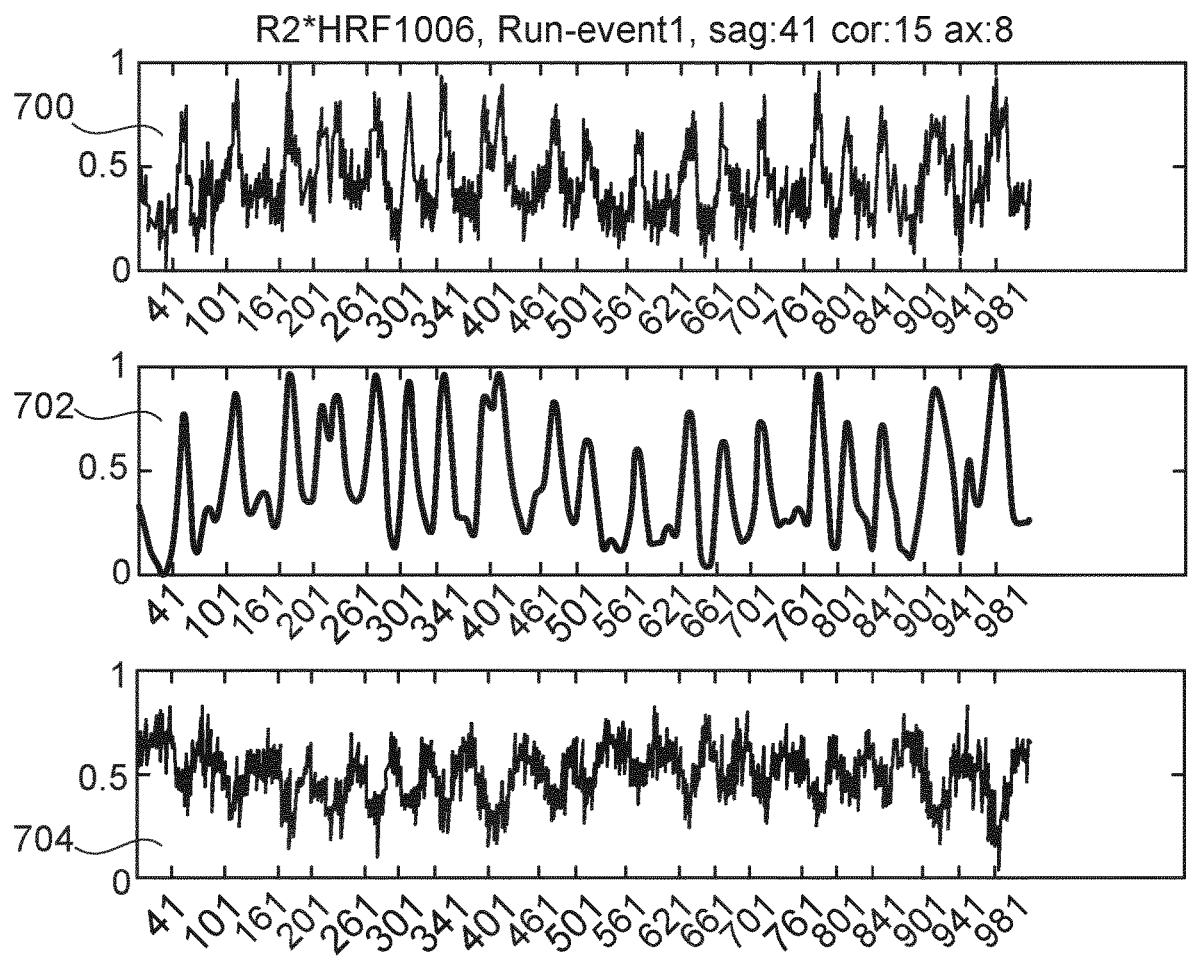
FIG. 7 shows the event-related R2-star data for a seed voxel selected in FIG. 6.

FIG. 7 shows the event-related R2-star data for the seed voxel 126 selected in FIG. 6. The curve 700 shows the raw data. Curve 702 shows the same data in curve 700 but with a moving algorithm or denoising algorithm applied to it. The curve 704 shows the difference between curves 700 and 702 and illustrates the noise that was removed.

Next, to determine the activation region 132 of the brain volume 500, a Pearson's correlation coefficient between the smooth voxels 702 and all of the smooth voxels in the four-dimensional dataset of the fMRI data is calculated.

4) Determine the Pearson's correlation coefficient of the smoothed voxels with all other smoothed voxels in the 4D dataset of the event-related data in FIGS. 8 and 9 below.

Figure 8:
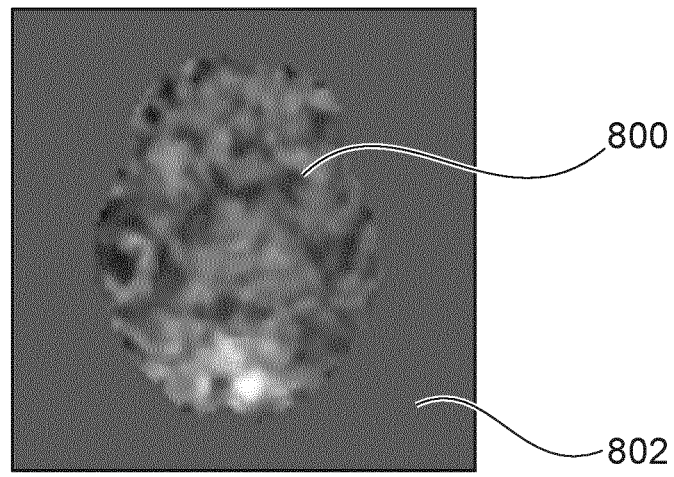
FIG. 8 shows the Pearson correlation coefficients for one slice of the brain volume.
Figure 9:
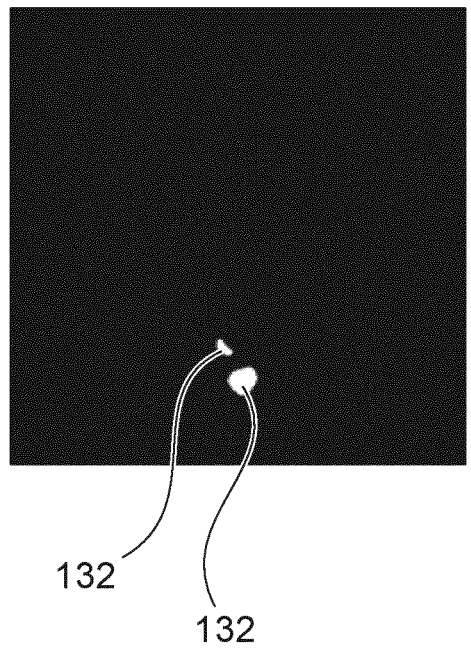
FIG. 9 illustrates an example of an activation region.

FIG. 8 shows an image of the Pearson correlation coefficients 800 for one slice at one time period of the R2-star map for the brain volume. The Pearson correlation coefficients 800 is visible in the center and the region 802 surrounding it has been masked off. By thresholding the Pearson's correlation 800, the activation region 132 has been identified and is displayed in FIG. 9. FIG. 9 was produced by thresholding FIG. 8.

Figure 10:
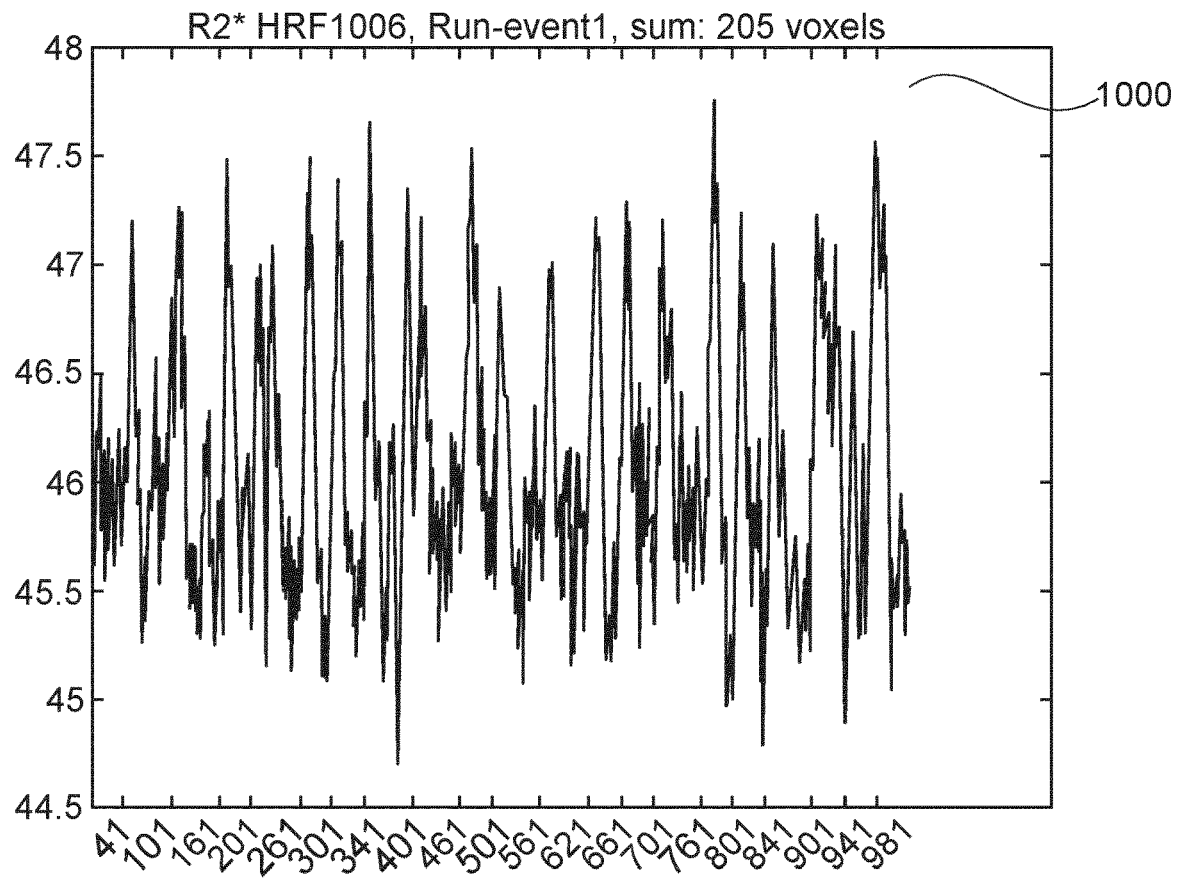
FIG. 10 shows the sum of the R2-star value for all of the activation regions depicted in FIG. 9.

5) Apply a threshold (0.75) and select the voxels from original unsmoothed data. Detrend (5th order) the time courses and average. FIG. 10 shows the sum of the R2-star value for all of the activation regions 132 depicted in FIG. 9. This is a spatially averaged signal 1000.

6) Select the HRF-responses with a window of −5 to 20 sec. Onset of the stimulus is at 0 sec. Average all selected HRF responses, FIG. 11. All individual responses (unsmoothed) are saved for further analysis.

Figure 11:
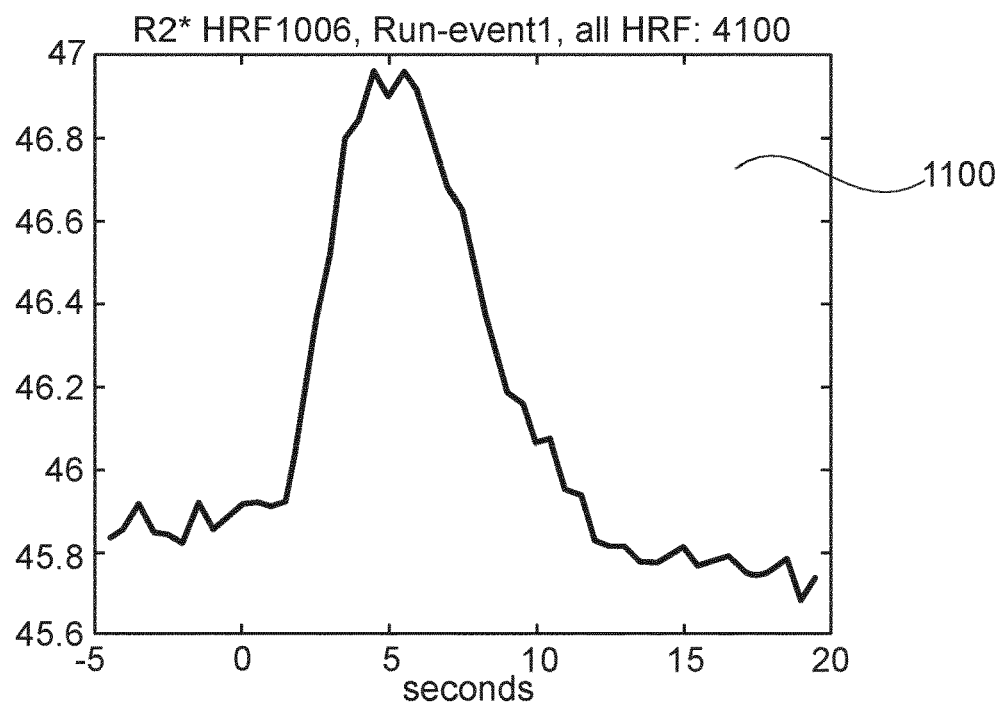
FIG. 11 depicts a hemodynamic response function.

FIG. 11 depicts a hemodynamic response function 1100 calculated by adding the HRF taken from the curve 1000 in FIG. 10, using the select criteria described just above. There are 106 voxels with 20 HRF responses per voxels. This gives 4100 responses that are added to construct the HRF 1100.

7) Fit a smoothing spline (again) to all the individual responses saved in step 5. Determine the time maximum and make a histogram, see FIG. 12.

Figure 12:
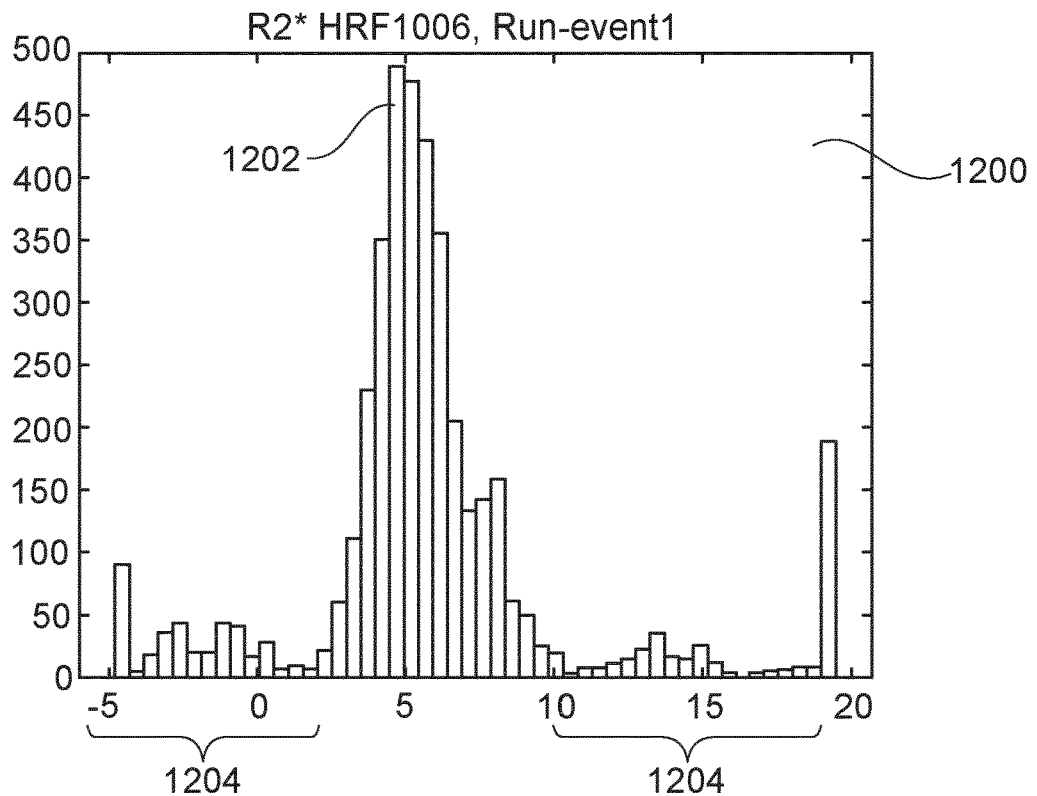
FIG. 12 shows a histogram 1200 of the maximum of the hemodynamic response functions.

FIG. 12 shows a histogram 1200 of the maximum of the 4100 hemodynamic response functions individually. Within this figure there can be seen a maximum value 1202 and a number of outliers 1204. Before proceeding, the hemodynamic response functions in the regions labeled 1204 are removed from the analysis; this removes the outliers. In this example a histogram was used to select the outliers but other values such as going within a certain number of standard deviations of the maximum 1202 would also function well.

8) Select the HRF responses around the maximum in the histogram, window: −1.5-+2.0 sec. Sum the selected unsmoothed HRF responses. Save the sum (mean) for further analysis, FIG. 13.

Figure 13:
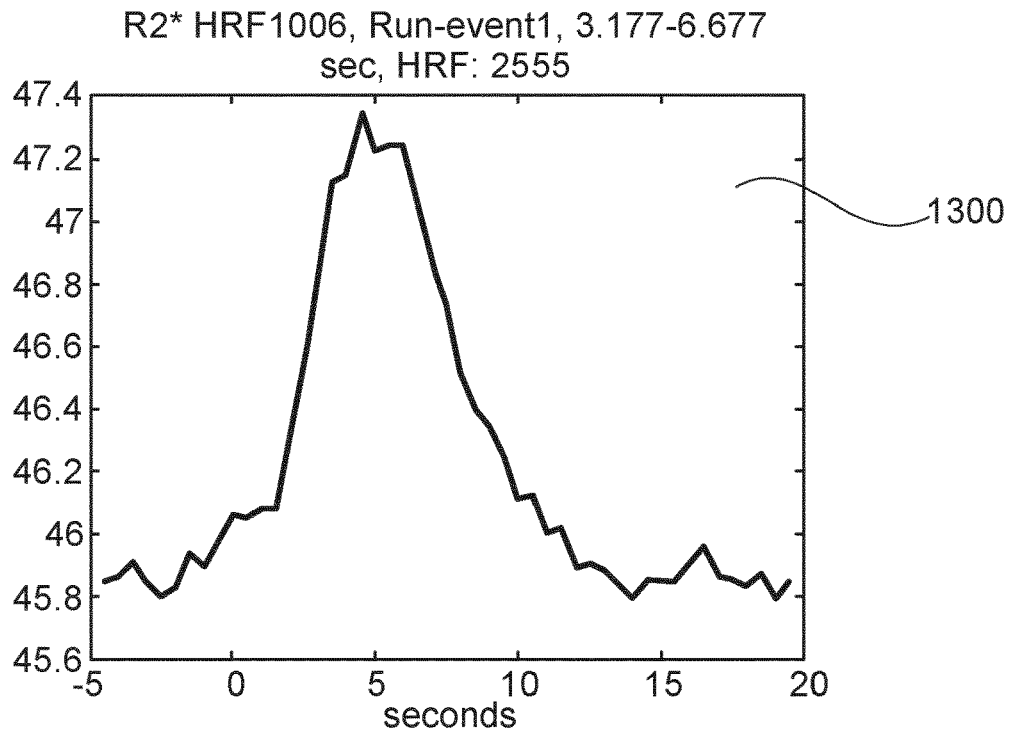
FIG. 13 shows an average hemodynamic response function.

FIG. 13 shows an average hemodynamic response function 1300 calculated from the average of the 2555 hemodynamic response functions that "survived" selection based on the histogram 1200 depicted in FIG. 12. The hemodynamic response function 1300 still shows some noise and is relatively rough. The hemodynamic response function (HRF) 1300 can for example be denoised or fit to a spline function.

Per subject analysis of the HRF-response

A smoothing spline may be to the sum. All further processing and analysis is done on the smoothed HRF.

For each HRF the maximum R2-star is determined from the smoothed curve. The signal value at the onset of the event (t=0) is taken as reference. The percentage-signal-change (PSC) is calculated with respect to the reference to provide the HRF curve as PSC.

Figure 14:
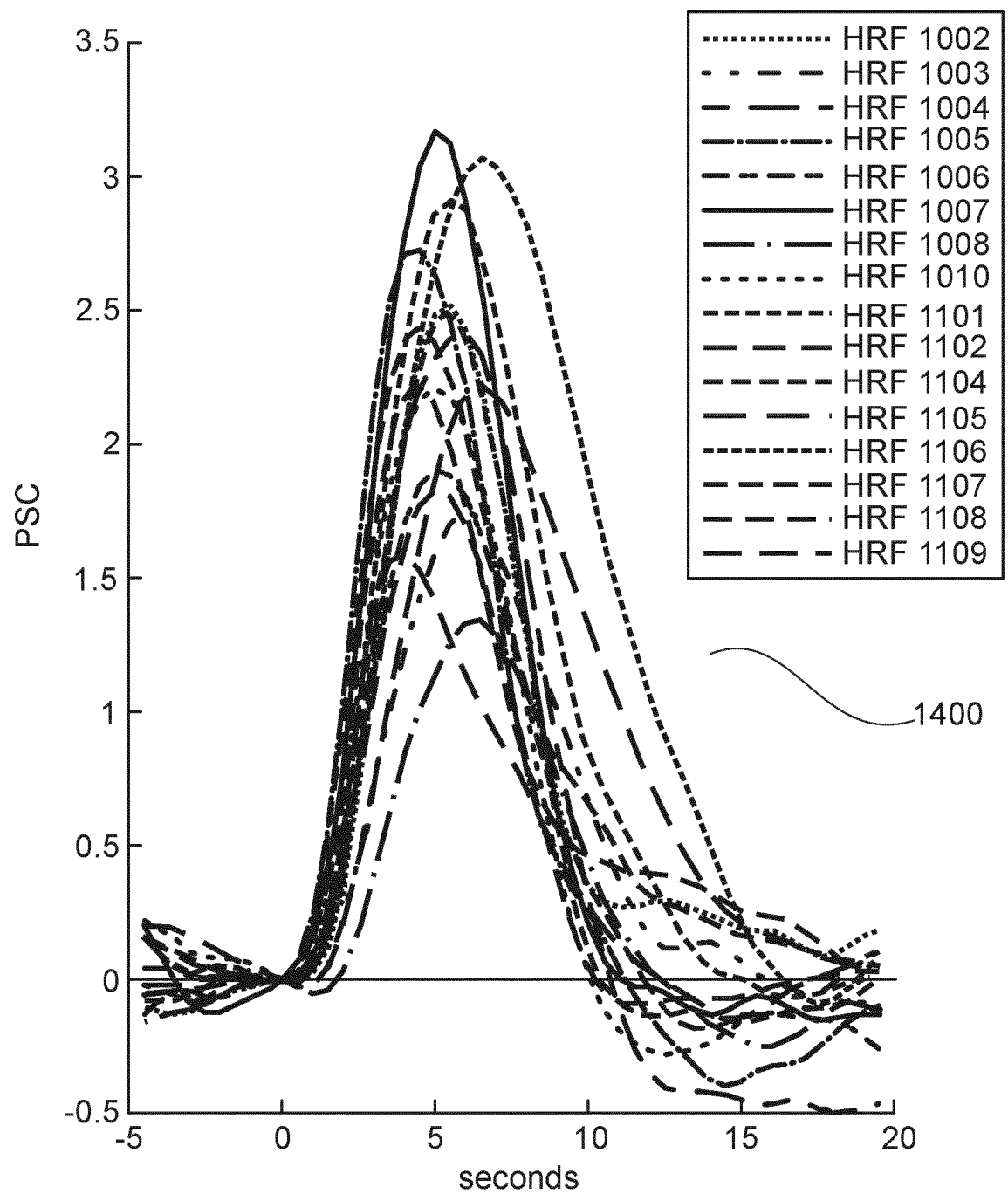
FIG. 14 illustrates the subject-specific hemodynamic response function for multiple individuals.

An example of HRF curves found is shown in FIG. 14

FIG. 14 illustrates the subject-specific hemodynamic response function for multiple individuals 1400. These subject-specific hemodynamic response functions are labeled HRF 1002 through HRF 1108, HRF 1110, and HRF 1101 through HRF 1109. As illustrated in FIG. 14, it can be seen that the subject-specific hemodynamic response function 1400 varies greatly for different individuals and it also illustrates the advantage of using a subject-specific hemodynamic response function 1400 when performing other functional magnetic resonance imaging protocols.

Several parameters of the theses HRF responses can be determined:

Maximum amplitude (PSC max).
Time to maximum
The width of the response (FWHM)
The skewness of the response
Integral of the response
The initial maximum rising slope (slope 1)
The maximum descending slope (slope 2)

An example is shown in the table below. The data are an analysis of the HRF responses shown in FIG. 14.

|  | mean | std |
| --- | --- | --- |
| Time to max | 5.31 | 0.80 |
| max PSC | 2.30 | 0.53 |
| FWHM | 5.55 | 0.74 |
| skew | 0.35 | 0.38 |
| integral | 25.62 | 8.60 |
| slope 1 | 0.39 | 0.09 |
| slope 2 | −0.26 | 0.09 |

The following illustrates the advantage of multi-echo fMRI. Both R2-star data and echo-2 data (determination of the HRF using just 2 echoes) were analyzed. Echo-2 is recorded at a TE of 28 ms, which is representative of the studies using single echo fMRI. For both data sets the same processing as derived above was used. The max PSC for both data sets was determined an is shown in FIG. 15 below.

Figure 15:
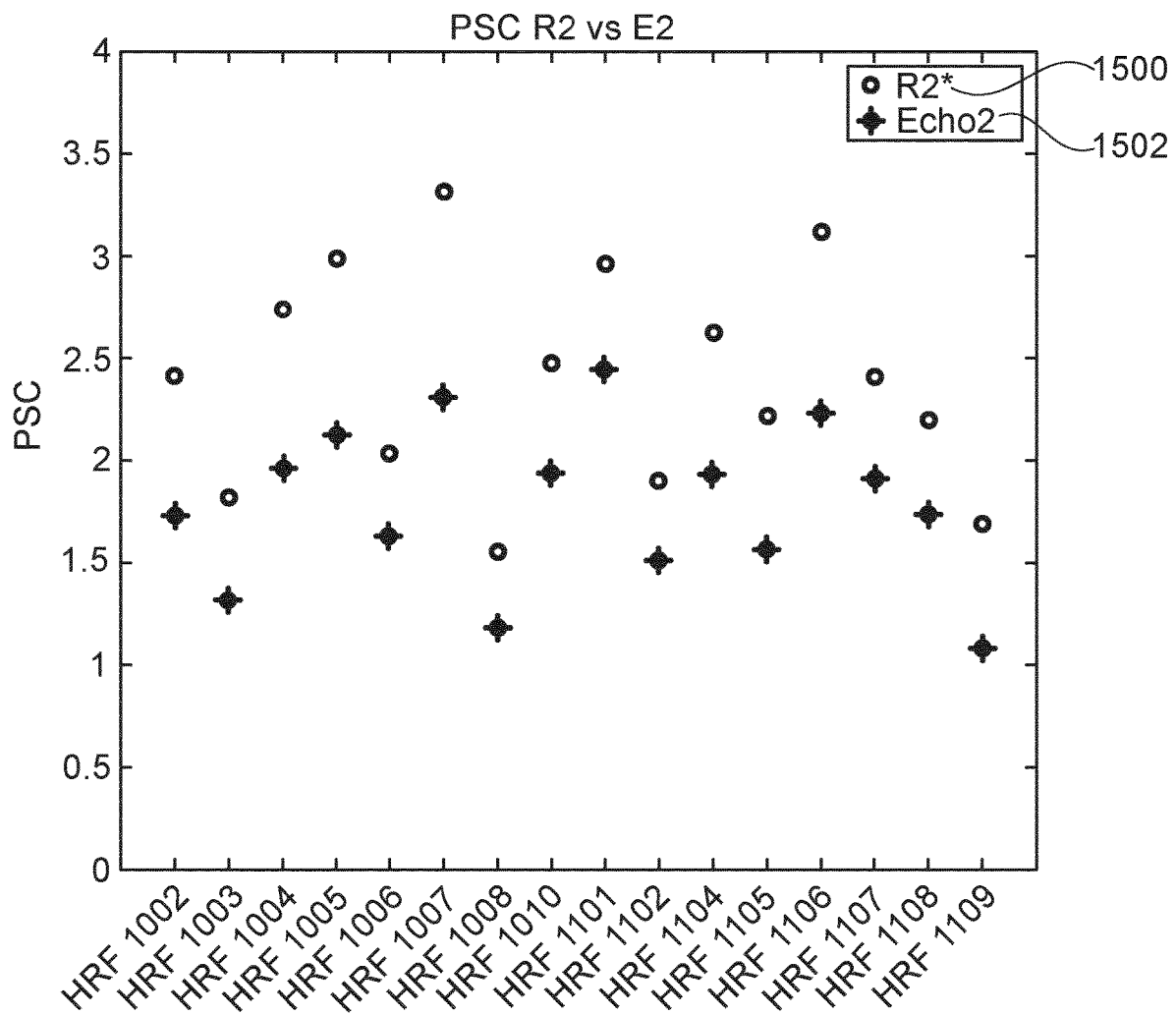
FIG. 15 illustrates the advantage of using a three-point measurement to determine the R2-star value.

FIG. 15 illustrates the advantage of using a three-point measurement to determine the R2-star value. In FIG. 15 an analysis using the three-point R2-star value 1500, as described herein, and also using the second echo at a time of 28 ms, which is very typical or representative of studies using single-echo functional magnetic resonance imaging, both datasets have the same data processing as derived above was used. The maximum percent change for both datasets was determined as is shown in FIG. 15. Each R2-star value 1500 is above the second echo 1502 data. It can be seen that there is a systematic error in using the single-echo functional magnetic resonance imaging technique. The average difference between the R2-star data and echo-2 is 34%

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE SIGNS LIST 100 medial system
102 computer
104 computational system
106 hardware interface

| REFERENCE SIGNS LIST | |
|---|---|
| 108 | user interface |
| 110 | memory |
| 120 | machine executable instructions |
| 122 | time series of a R2-star map |
| 124 | stimulus signal |
| 126 | selection of one or more seed voxels |
| 128 | denoised time series of the R2-star map |
| 130 | correlation maps |
| 132 | activation region of the brain volume |
| 134 | hemodynamic response functions |
| 136 | subject specific hemodynamic response function |
| 200 | receive a time series of a R2-star map for a brain volume of a subject |
| 202 | receive a stimulus signal descriptive of an occurrence of a sensory stimulus repeatedly provided to the subject |
| 204 | receive a selection of one or more seed voxels identified in the time series of the R2-star map |
| 206 | calculate a denoised time series of the R2-star map by applying a temporal filter algorithm to the time series of the R2-star map |
| 208 | calculate a correlation map for each voxel of the one or more seed voxels by calculating a pixel wise correlation between each voxel of the one or more seed voxels and the denoised time series of the R2-star map |
| 210 | determine an activated region of the brain volume by combining voxels identified in the correlation map for each voxel of the one or more seed voxels above a predetermined threshold |
| 212 | provide a hemodynamic response function for each voxel and each occurrence of the sensory stimulus in the activated region of the brain volume by aligning the time series of the R2-star map with the stimulus signal |
| 214 | provide a subject specific hemodynamic response function by averaging the hemodynamic response function for each voxel and each occurrence of the sensory stimulus in the activated region of the brain volume |
| 300 | medical system |
| 302 | magnetic resonance imaging system |
| 304 | magnet |
| 306 | bore of magnet |
| 308 | imaging zone |
| 309 | field of view |
| 310 | magnetic field gradient coils |
| 312 | magnetic field gradient coil power supply |
| 314 | head coil |
| 316 | transceiver |
| 318 | subject |
| 320 | subject support |
| 322 | stimulus system (display) |
| 330 | EPI multi-echo pulse sequence commands |
| 332 | T1 weighted pulse sequence commands |
| 334 | EPI multi-echo T2-star weighted k-space data |
| 336 | T1 weighted k-space data |
| 338 | T1 weighted image of brain volume |
| 340 | T2-star weighted image for each echo |
| 342 | aligned T2-star weighted image for each echo |
| 400 | acquire the T1 weighted k-space data by controlling the magnetic resonance imaging system with the T1 weighted pulse sequence commands |
| 402 | acquire the multiple acquisitions of EPI multi-echo T2-star weighted k-space data by controlling the magnetic resonance imaging system with the EPI multi-echo pulse sequence commands |
| 404 | control the stimulus system with the stimulus signal during the acquisition of the multiple acquisitions of EPI multi-echo T2-star weighted k-space data |
| 406 | reconstruct a T1 weighted image of the brain volume from the T1 weighted k-space data |
| 408 | reconstruct a T2-star weighted image for each echo of the multiple acquisitions of EPI multi-echo T2-star weighted k-space data |
| 410 | calculate an aligned T2-star weighted image for each echo of the multiple acquisitions of EPI multi-echo T2-star weighted k-space data by performing preprocessing that aligns the T2-star weighted image for each echo of the multiple acquisitions of EPI multi-echo T2-star weighted k-space data with the T1 weighted image of the brain volume |

| REFERENCE SIGNS LIST | |
|---|---|
| 412 | calculate the time series of the R2-star map for the brain volume of the subject for each voxel by fitting a decay curve to the aligned T2-star weighted image for each echo of the multiple acquisitions of EPI multi-echo T2-star weighted k-space data |
| 500 | brain volume |
| 600 | first view of R2-star image |
| 602 | second view of R2-star image |
| 604 | third view of R2-star image |
| 700 | event related R2-star time series for seed voxel |
| 702 | smoothed version of 700 |
| 704 | difference between 700 and 702 |
| 800 | Pearson correlation coefficients for (1 slice) of brain volume |
| 802 | masked region |
| 1000 | spatially averaged signal |
| 1100 | hemodynamic response function |
| 1200 | histogram of maximum of hemodynamic functions |
| 1202 | maximum |
| 1204 | outliers |
| 1300 | averaged hemodynamic function |
| 1400 | subject specific hemodynamic functions for multiple individuals |

The invention claimed is:

1. A medical system comprising:
a memory storing machine executable instructions;
a computational system, wherein execution of the machine executable instructions causes the computational system to:
receive a time series of a R2-star map for a brain volume of a subject;
receive a stimulus signal descriptive of an occurrence of a sensory stimulus repeatedly provided to the subject, wherein the stimulus signal is synchronized to the time series of the R2-star map;
receive a selection of one or more seed voxels identified in the time series of the R2-star map;
calculate a denoised time series of the R2-star map by applying a temporal filter algorithm to the time series of the R2-star map;
calculate a correlation map for each voxel of the one or more seed voxels by calculating a pixel wise correlation between each voxel of the one or more seed voxels in the time series of the R2-star map and the denoised time series of the R2-star map;
determine an activated region of the brain volume by combining voxels identified in the correlation map for each voxel of the one or more seed voxels above a predetermined threshold;
provide a hemodynamic response function for each voxel and each occurrence of the sensory stimulus in the activated region of the brain volume by aligning the time series of the R2-star map with the stimulus signal; and
provide a subject specific hemodynamic response function by averaging the hemodynamic response function for each voxel and each occurrence of the sensory stimulus in the activated region of the brain volume.

2. The medical system of claim 1, wherein execution of the machine executable instructions further causes the computational system to:
calculate a time of maximum value for the hemodynamic response function for each voxel and each occurrence of the sensory stimulus in the activated region of the brain volume;
calculate a statistical property of the time of maximum value for the hemodynamic response function for each voxel and each occurrence of the sensory stimulus in the activated region of the brain volume;

remove any hemodynamic response function from the calculation of the subject specific hemodynamic response function if it fails to meet a criteria determined using the statistical property.

3. The medical system of claim 2, wherein the time of maximum value for the hemodynamic response function for each voxel and each occurrence of the sensory stimulus in the activated region of the brain volume is calculated using a smoothing function.

4. The medical system of claim 1 wherein execution of the machine executable instructions further causes the computational system to:

receive multiple acquisitions of EPI multi-echo T2-star weighted k-space data descriptive of the brain volume of the subject, wherein the multiple acquisitions are synchronized to the stimulus signal;

receive T1 weighted k-space data descriptive of the brain volume of the subject;

reconstruct a T1 weighted image of the brain volume from the T1 weighted k-space data;

reconstruct a T2-star weighted image for each echo of the multiple acquisitions of EPI multi-echo T2-star weighted k-space data; and calculate an aligned T2-star weighted image for each echo of the multiple acquisitions of EPI multi-echo T2-star weighted k-space data by performing preprocessing that aligns the T2-star weighted image for each echo of the multiple acquisitions of EPI multi-echo T2-star weighted k-space data with the T1 weighted image of the brain volume with each other;

calculate the time series of the R2-star map for the brain volume of the subject for each voxel by fitting a decay curve to the aligned T2-star weighted image for each echo of the multiple acquisitions of EPI multi-echo T2-star weighted k-space data.

5. The medical system of claim 4, wherein the calculation of the aligned T2-star weighted image for each echo of the multiple acquisitions of EPI multi-echo T2-star weighted k-space data is performed by preprocessing that aligns the T2-star weighted image for each echo of the multiple acquisitions of EPI multi-echo T2-star weighted k-space data with the T1 weighted image of the brain volume with each other comprises:

co-registering a chosen image corresponding to a first echo of a chosen acquisition of the multiple acquisitions of EPI multi-echo T2-star weighted k-space data to the T1 weighted image;

segmenting the T1 weighted image to produce a grey matter segmentation, a white matter segmentation, and a cerebral spinal fluid segmentation;

reslice the T1 weighted image, the grey matter segmentation, the white matter segmentation, and the cerebral spinal fluid segmentation to match the chosen image using the co-registration between the chosen image and the T1 weighted image;

construct a brain mask using the grey matter segmentation, the white matter segmentation, and the cerebral spinal fluid segmentation; and realign the T2-star weighted image for each echo of the multiple acquisitions of EPI multi-echo with a corresponding image of the chosen image.

6. The medical system of claim 4, wherein the EPI multi-echo T2-star weighted k-space data descriptive of the brain volume of the subject has k-space data for three echoes.

7. The medical system of claim 1, wherein the memory further stores EPI multi-echo pulse sequence commands and T1 weighted pulse sequence commands, wherein the medical system further comprises:

a magnetic resonance imaging system; and a stimulus system configured to provide the sensory stimulus to the subject;

wherein execution of the machine executable instructions are further configured to cause the computational system to:

acquire the T1 weighted k-space data by controlling the magnetic resonance imaging system with the T1 weighted pulse sequence commands;

acquire the multiple acquisitions of EPI multi-echo T2-star weighted k-space data by controlling the magnetic resonance imaging system with the EPI multi-echo pulse sequence commands; and control the stimulus system with the stimulus signal during the acquisition of the multiple acquisitions of EPI multi-echo T2-star weighted k-space data.

8. The medical system of claim 7, wherein the stimulus system is a visual stimulus system, and wherein the brain volume comprises the visual cortex.

9. The medical system of claim 7 wherein EPI multi-echo pulse sequence commands are single shot EPI pulse sequence commands, wherein the EPI multi-echo pulse sequence commands are multi-band pulse sequence commands.

10. The medical system of claim 1, wherein execution of the machine executable instructions further causes the computational system to calculate at least one of the following parameters from the subject specific hemodynamic response function: a maximum amplitude, a time to maximum amplitude, a FWHM width of the subject specific hemodynamic response function, a skewness of the subject specific hemodynamic response function, an integral of the subject specific hemodynamic response function, an initial maximum rising slope, or a maximum descending slope.

11. The medical system of claim 1, wherein execution of the machine executable instructions further causes the computational system to:

receive functional Magnetic Resonance Imaging k-space data descriptive of a brain region of the subject; and calculate a functional magnetic resonance image using the functional Magnetic Resonance Imaging k-space data and the subject specific hemodynamic response function.

12. The medical system of claim 1, wherein execution of the machine executable instructions further causes the computational system to:

construct a percentage change mapping from the R2-star map using the stimulus signal;

provide the one or more seed voxels by searching for voxels above a predetermined threshold within the percentage change mapping.

13. The medical system of claim 1, wherein the time series of a R2-star map comprises block related R2-star maps, wherein execution of the machine executable instructions causes the computational system to identify the one or more seed voxels by:

construct a percentage change mapping from the block related R2-star maps by calculating a change between resting blocks and stimulus blocks;

provide the one or more seed voxels by searching for voxels above a predetermined threshold within the percentage change mapping.

14. A method of medical imaging, wherein the method comprises:
  receiving a time series of a R2-star map for a brain volume of a subject;
  receiving a stimulus signal descriptive of an occurrence of a sensory stimulus repeatedly provided to the subject, wherein the stimulus signal is synchronized to the time series of the R2-star map;
  receiving a selection of one or more seed voxels identified in the time series of the R2-star map;
  calculating a denoised time series of the R2-star map by applying a temporal filter algorithm to the time series of the R2-star map;
  calculating a correlation map for each voxel of the one or more seed voxels by calculating a pixel wise correlation between each voxel of the one or more seed voxels in the time series of the R2-star map and the denoised time series of the R2-star map;
  determining an activated region of the brain volume by combining voxels identified in the correlation map for each voxel of the one or more seed voxels above a predetermined threshold;
  providing a hemodynamic response function for each voxel and each occurrence of the sensory stimulus in the activated region of the brain volume by aligning the time series of the R2-star map with the stimulus signal; and
  providing a subject specific hemodynamic response function by averaging the hemodynamic response function for each voxel and each occurrence of the sensory stimulus in the activated region of the brain volume.

15. The method of claim 14 further comprising:
  calculating a time of maximum value for the hemodynamic response function for each voxel and each occurrence of the sensory stimulus in the activated region of the brain volume;
  calculating a statistical property of the time of maximum value for the hemodynamic response function for each voxel and each occurrence of the sensory stimulus in the activated region of the brain volume;
  removing any hemodynamic response function from the calculation of the subject specific hemodynamic response function if it fails to meet a criteria determined using the statistical property.

16. The method of claim 14, wherein the time of maximum value for the hemodynamic response function for each voxel and each occurrence of the sensory stimulus in the activated region of the brain volume is calculated using a smoothing function.

17. The method of claim 14, further comprising:
  receiving multiple acquisitions of EPI multi-echo T2-star weighted k-space data descriptive of the brain volume of the subject, wherein the multiple acquisitions are synchronized to the stimulus signal;
  receiving T1 weighted k-space data descriptive of the brain volume of the subject;
  reconstructing a T1 weighted image of the brain volume from the T1 weighted k-space data;
  reconstructing a T2-star weighted image for each echo of the multiple acquisitions of EPI multi-echo T2-star weighted k-space data; and
  calculating an aligned T2-star weighted image for each echo of the multiple acquisitions of EPI multi-echo T2-star weighted k-space data by performing preprocessing that aligns the T2-star weighted image for each echo of the multiple acquisitions of EPI multi-echo T2-star weighted k-space data with the T1 weighted image of the brain volume with each other;
  calculating the time series of the R2-star map for the brain volume of the subject for each voxel by fitting a decay curve to the aligned T2-star weighted image for each echo of the multiple acquisitions of EPI multi-echo T2-star weighted k-space data.

18. The method of claim 17 further including:
  wherein the calculation of the aligned T2-star weighted image for each echo of the multiple acquisitions of EPI multi-echo T2-star weighted k-space data is performed by preprocessing that aligns the T2-star weighted image for each echo of the multiple acquisitions of EPI multi-echo T2-star weighted k-space data with the T1 weighted image of the brain volume with each other includes:
  co-registering a chosen image corresponding to a first echo of a chosen acquisition of the multiple acquisitions of EPI multi-echo T2-star weighted k-space data to the T1 weighted image;
  segmenting the T1 weighted image to produce a grey matter segmentation, a white matter segmentation, and a cerebral spinal fluid segmentation;
  reslicing the T1 weighted image, the grey matter segmentation, the white matter segmentation, and the cerebral spinal fluid segmentation to match the chosen image using the co-registration between the chosen image and the T1 weighted image;
  constructing a brain mask using the grey matter segmentation, the white matter segmentation, and the cerebral spinal fluid segmentation; and
  realigning the T2-star weighted image for each echo of the multiple acquisitions of EPI multi-echo with a corresponding image of the chosen image.

19. A computer program comprising machine executable instructions, stored on a non-transitory computer readable medium, configured for execution by a computational system, wherein execution of the machine executable instructions causes the computational system to:
  receive a time series of a R2-star map for a brain volume of a subject;
  receive a stimulus signal descriptive of an occurrence of a sensory stimulus repeatedly provided to the subject, wherein the stimulus signal is synchronized to the time series of the R2-star map;
  receive a selection of one or more seed voxels identified in the time series of the R2-star map;
  calculate a denoised time series of the R2-star map by applying a temporal filter algorithm to the time series of the R2-star map;
  calculate a correlation map for each voxel of the one or more seed voxels by calculating a pixel wise correlation between each voxel of the one or more seed voxels in the time series of the R2-star map and the denoised time series of the R2-star map;
  determine an activated region of the brain volume by combining voxels identified in the correlation map for each voxel of the one or more seed voxels above a predetermined threshold;
  provide a hemodynamic response function for each voxel and each occurrence of the sensory stimulus in the activated region of the brain volume by aligning the time series of the R2-star map with the stimulus signal; and
  provide a subject specific hemodynamic response function by averaging the hemodynamic response function for each voxel and each occurrence of the sensory stimulus in the activated region of the brain volume.

\* \* \* \* \*